(12) United States Patent
Motoki et al.

(10) Patent No.: US 10,672,972 B2
(45) Date of Patent: Jun. 2, 2020

(54) ULTRASONIC TRANSDUCER UNIT

(71) Applicant: Hitachi, Ltd., Tokyo (JP)

(72) Inventors: Kazuya Motoki, Tokyo (JP); Kazuhiro Kobayashi, Tokyo (JP); Toru Watanabe, Tokyo (JP)

(73) Assignee: HITACHI, LTD., Tokyo (JP)

( * ) Notice: Subject to any disclaimer, the term of this patent is extended or adjusted under 35 U.S.C. 154(b) by 337 days.

(21) Appl. No.: 15/551,304

(22) PCT Filed: Jan. 18, 2016

(86) PCT No.: PCT/JP2016/051286
§ 371 (c)(1),
(2) Date: Aug. 16, 2017

(87) PCT Pub. No.: WO2016/136327
PCT Pub. Date: Sep. 1, 2016

(65) Prior Publication Data
US 2018/0040805 A1 Feb. 8, 2018

(30) Foreign Application Priority Data
Feb. 27, 2015 (JP) ................................. 2015-038544

(51) Int. Cl.
*H01L 41/113* (2006.01)
*G01S 7/521* (2006.01)
(Continued)

(52) U.S. Cl.
CPC .............. *H01L 41/113* (2013.01); *A61B 8/14* (2013.01); *G01S 7/521* (2013.01); *H01L 41/09* (2013.01); *H04R 17/00* (2013.01); *H04R 17/10* (2013.01)

(58) Field of Classification Search
CPC combination set(s) only.
See application file for complete search history.

(56) References Cited

U.S. PATENT DOCUMENTS 5,872,493 A * 2/1999 Ella .......................... H03H 3/02
310/322
6,603,241 B1 8/2003 Barber et al.
(Continued)

FOREIGN PATENT DOCUMENTS

| CN | 101238754 A | 8/2008 |
| CN | 101878658 A | 11/2010 |

(Continued)

OTHER PUBLICATIONS

International Search Report received for PCT Patent Application No. PCT/JP2016/051286, dated Apr. 5, 2016, 2 pages.
(Continued)

*Primary Examiner* — Thomas M Dougherty
*Assistant Examiner* — Karen B Addison
(74) *Attorney, Agent, or Firm* — Baker Botts L.L.P.

(57) ABSTRACT

A resonance layer (30) and an acoustic separation layer (34) are arranged adjacent to each other between a piezoelectric element (24) and a circuit board (16) provided with an electronic circuit for driving the piezoelectric element. The acoustic impedance of the resonance layer (30) is higher than that of the piezoelectric element (24), and the acoustic impedance of the acoustic separation layer (34) is lower than that of the circuit board (16). An ultrasonic wave is reflected at the interface between the resonance layer (30) and the acoustic separation layer (34) where the difference in acoustic impedance is large, and the ultrasonic wave propagating to the circuit-board (16) side is reduced.

7 Claims, 3 Drawing Sheets

(51) Int. Cl.
    *H01L 41/09*     (2006.01)
    *H04R 17/00*     (2006.01)
    *A61B 8/14*      (2006.01)
    *H04R 17/10*     (2006.01)

(56)           References Cited

U.S. PATENT DOCUMENTS

2003/0028108 A1    2/2003   Miller
2009/0301200 A1*  12/2009   Tanaka .................. B06B 1/0292
                                                              73/603
2010/0242612 A1    9/2010   Sano et al.
2013/0293066 A1   11/2013   Tsuzuki et al.
2015/0216509 A1    8/2015   Yamagata et al.

FOREIGN PATENT DOCUMENTS

CN        102598330  A      7/2012
CN        103210665  A      7/2013
JP         10-270979 A     10/1998
JP        2002-041052 A     2/2002
JP        2005-507581 A     3/2005
WO        2011028430 A1     3/2011
WO        2014054810 A1     4/2014

OTHER PUBLICATIONS

Chinese Office Action dated Jun. 3, 2019 in CN 201680011506.X with machine translation.

* cited by examiner

ULTRASONIC TRANSDUCER UNIT

CROSS-REFERENCE TO RELATED APPLICATIONS

This application is a national phase claiming the benefit of and priority to International Patent Application No. PCT/JP2016/051286, entitled "ULTRASONIC TRANSDUCER UNIT", filed Jan. 18, 2016 which claims priority to Japanese Patent Application No. 2015-038544, filed Feb. 27, 2015, which are hereby incorporated by reference in their entireties.

TECHNICAL FIELD

The present disclosure relates to an ultrasound transducer unit used for an ultrasound probe, and in particular, to a structure of the ultrasound transducer unit.

BACKGROUND

Ultrasound diagnostic apparatuses are used in the medical field. An ultrasound diagnostic apparatus is an apparatus which transmits and receives ultrasound to and from a living body, and forms an ultrasound image based on a reception signal obtained by the transmission and reception of the ultrasound. The transmission and reception of the ultrasound to and from the living body are executed by an ultrasound probe (probe). The probe includes a transducer including a piezoelectric element, and ultrasound is transmitted and received by driving the piezoelectric element.

The transducer includes a matching layer placed on a living body side of the piezoelectric element. The matching layer is a layer for acoustically matching the piezoelectric element and the living body, by gradationally reducing an acoustic impedance from the piezoelectric element toward the living body. In addition, the transducer may include a resonance layer placed adjacent to a back surface of the piezoelectric element; that is, a surface opposite from the living body side. An acoustic impedance of the resonance is higher than that of the piezoelectric element, and is useful for resonating with the piezoelectric element to effectively transmit the ultrasound toward the living body. On a back surface of the transducer, a circuit board having an electronic circuit which drives the piezoelectric element is placed. Patent Document 1 shows an example of the ultrasound probe.

CITATION LIST

Patent Literature
  Patent Document 1: JP 2005-507581 A

SUMMARY

Technical Problem

When the ultrasound transmitted from the transducer propagates to the circuit board, the ultrasound is reflected within the circuit board, and a part of the ultrasound returns to the transducer and is further transmitted into the living body. The ultrasound reflected in the circuit board is transmitted in a delayed manner from the ultrasound which is directly transmitted. Due to the delay, the ultrasound may form noise, resulting in a possible degradation of the ultrasound image.

An advantage of the present disclosure lies in reduction of the ultrasound propagating from the transducer to the circuit board side.

Solution to Problem

According one aspect of the present disclosure, there is provided an ultrasound transducer unit comprising: a piezoelectric element; a circuit board having an electronic circuit which drives the piezoelectric element; a resonance layer placed between the piezoelectric element and the circuit board, and being higher in acoustic impedance than the piezoelectric element; and an acoustic separation layer placed on a circuit board side of the resonance layer and adjacent to the resonance layer, and being lower in acoustic impedance than the circuit board.

Due to the difference in the acoustic impedance between the resonance layer and the acoustic separation layer, the ultrasound may be reflected at a boundary surface between these layers, and, consequently, propagation of the ultrasound to the circuit board side can be suppressed.

According to another aspect of the present disclosure, the acoustic separation layer may comprise a porous material, in particular, porous carbon.

According to another aspect of the present disclosure, the acoustic impedance of the resonance layer may be greater than or equal to 2.3 times the acoustic impedance of the piezoelectric element, and the acoustic impedance of the acoustic separation layer may be less than or equal to $\frac{1}{20}$ of the acoustic impedance of the circuit board. According to another aspect of the present disclosure, the acoustic impedance of the acoustic separation layer may be $\frac{1}{70}$ the acoustic impedance of the resonance layer.

Advantageous Effects of Invention

According to various aspects of the present disclosure, the ultrasound can be reflected at the boundary surface between the acoustic separation layer and the resonance layer and propagation of the ultrasound to the circuit board can be suppressed. Consequently, the noise due to ultrasound reflected within the circuit board can be reduced.

DESCRIPTION OF EMBODIMENTS

Figure 1:
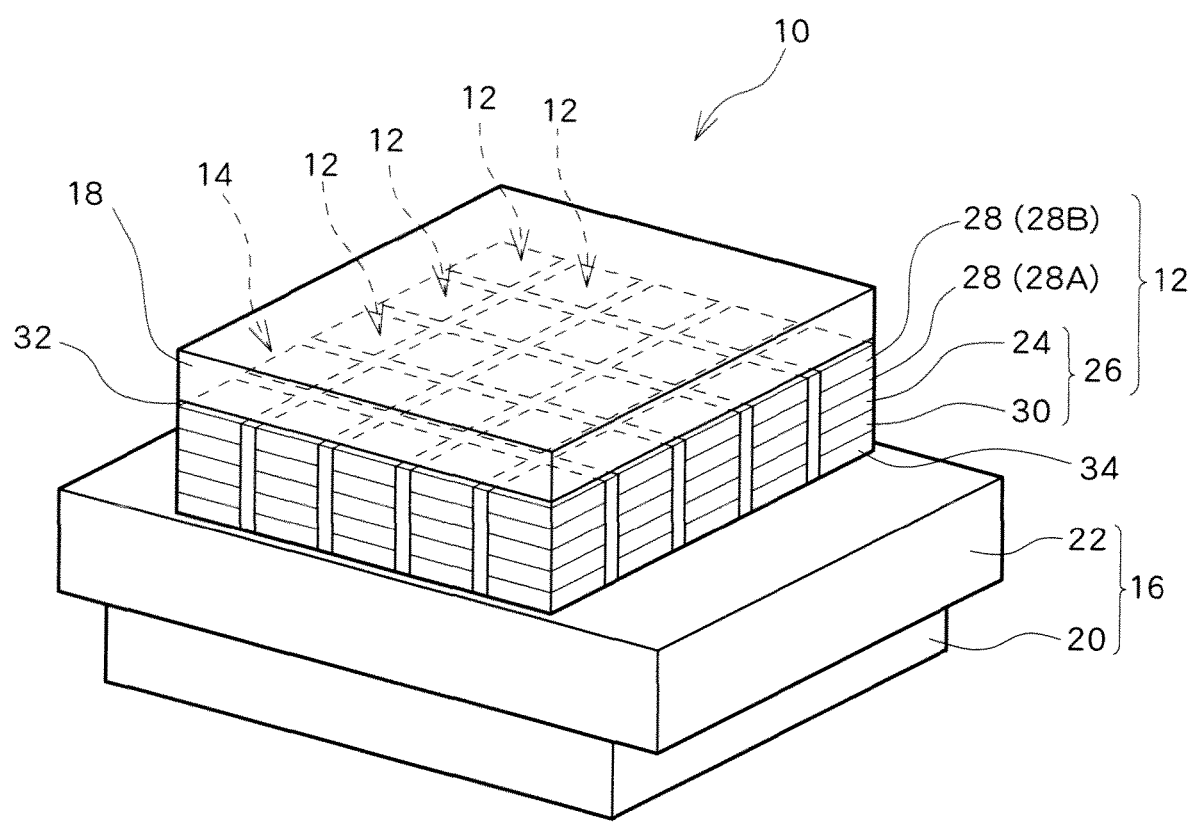
FIG. 1 is a perspective diagram schematically showing a structure of an ultrasound transducer unit according to an embodiment of the present disclosure.
Figure 2:
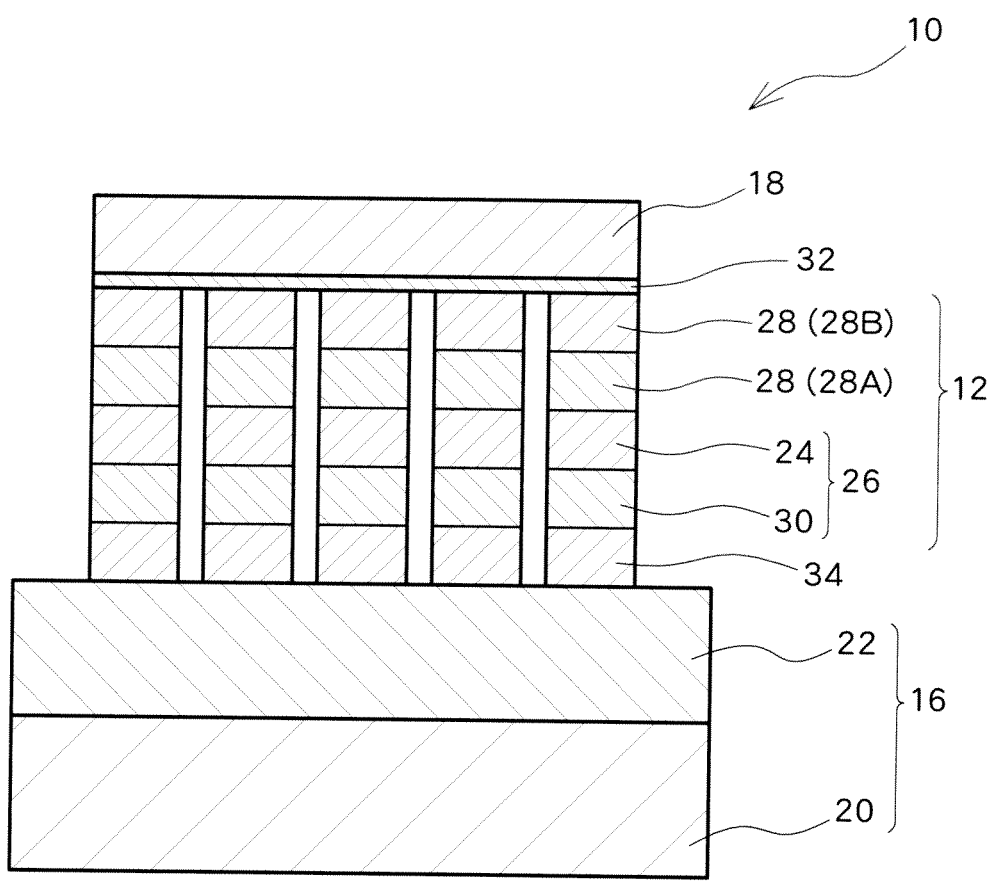
FIG. 2 is a cross-sectional diagram schematically showing a structure of an ultrasound transducer unit according to an embodiment of the present disclosure.

An embodiment of the present disclosure will now be described with reference to the drawings. FIG. 1 is a perspective diagram showing an ultrasound transducer unit 10 according to an embodiment of the present disclosure. FIG. 2 is a cross sectional diagram of the ultrasound transducer unit 10. The ultrasound transducer unit 10 is built in a probe of an ultrasound diagnostic apparatus, and transmits and receives ultrasound to and from a living body which the probe contacts. A transmission direction of the ultrasound in FIG. 1 is upward. In the following description, the terms related to an up-and-down relationship such as "upper" and "lower" merely describe the up-and-down relationship in the figures, and do not mean the up-and-down relationship in usage or the like.

The ultrasound transducer unit 10 includes a two-dimensional array transducer 14 in which individual transducers 12 are arranged vertically and horizontally. In the array transducer 14 shown in the figure, the same number of individual transducers 12 are arranged vertically and horizontally, to form an approximate square as a whole. In the figures, for the purpose of description, the number of the individual transducers 12 is set to 5×5=25, but the actual array transducer 14 includes many more individual transducers 12, for example, thousands of individual transducers 12. In this structure, an ultrasound beam can be scanned in an arbitrary angle. From data within a three-dimensional space captured by scanning of an arbitrary angle, a three-dimensional ultrasound image representing the three-dimensional space can be formed. Alternatively, from the data, an ultrasound image at an arbitrary cross section may be formed. Alternatively, the array transducer may be a one-dimensional array in which the individual transducers 12 are arranged in a straight line. Alternatively, the array transducer may be an approximate rectangular array in which different numbers of individual transducers 12 are arranged in the vertical direction and the horizontal direction.

The ultrasound transducer unit 10 has a circuit board 16 having an electronic circuit which drives the array transducer 14, and a protection layer 18 which covers and protects the array transducer 14. In the case of the ultrasound transducer unit 10, the circuit board 16 has an electronic circuit board 20 on which an electronic circuit is formed, and a relay board 22 having a wiring or a circuit for connecting the electronic circuit and the individual transducer 12. The relay board 22 may have a function to switch a connection between terminals on the electronic circuit and the individual transducers 12.

The individual transducer 12 includes a transducer element 26 including a piezoelectric element 24, and an acoustic matching layer 28. The transducer element 26 includes a resonance layer 30 in addition to the piezoelectric element 24. The resonance layer 30 is placed on a back side of the piezoelectric element 24; that is, on a side opposite from the direction of transmission and reception of the ultrasound. The resonance layer 30 is also higher in acoustic impedance than the piezoelectric element 24, and forms a hard back layer, and the piezoelectric element 24 and the resonance layer 30 as a whole transmit and receive the ultrasound. The acoustic impedances of the piezoelectric element 24 and the resonance layer 30 are, for example, 30 MRayl and 70 to 100 MRayl, respectively. The acoustic impedance of the resonance layer 30 is greater than or equal to 2.3 times the acoustic impedance of the piezoelectric element 24. A material of the resonance layer 30 is a resin material including a conductive filler such as carbon and tungsten, a metal, an alloy, a sintered structure of metal, a sintered structure of metal and an inorganic material, or a composite of these. The resonance layer 30 is useful in effectively transmitting the ultrasound to the living body by resonating with the piezoelectric element 24. The acoustic impedance of the circuit board 16, in particular, the relay board 22, is about 20 MRayl.

The acoustic matching layer 28 is a layer for acoustically matching the piezoelectric element 24 and the living body by gradationally reducing the acoustic impedance from the piezoelectric element 24 toward the living body. The acoustic matching layer 28 may be formed from only one layer, or may include a plurality of layers, in order to smoothly reduce the acoustic impedance toward the living body. In the example structure shown in the figures, the acoustic matching layer 28 includes two layers, a first acoustic matching layer 28A and a second acoustic matching layer 28B.

On a surface of the individual transducer 12 facing the protection layer 18, a ground electrode 32 common for all individual transducers 12 is joined. The acoustic matching layer 28 has conductivity, and electrically connects the ground electrode 32 and the transducer element 26. In the acoustic matching layer 28, in order to introduce conductivity, there may be used a resin to which glass-form carbon, carbon, a graphite material, or a conductive filler is mixed. The resin may be, for example, an epoxy resin.

On a back side of the resonance layer 30; that is, on the side of the circuit board 16, an acoustic separation layer 34 is placed adjacent to the resonance layer 30. The acoustic separation layer 34 is lower in acoustic impedance than the piezoelectric element 24 and the circuit board 16. The relay board 22 and the electronic circuit board 20 included in the circuit board 16 are approximately equal in acoustic impedance. However, when these impedances differ from each other, the acoustic impedance of the acoustic separation layer 34 is set lower than the acoustic impedance of the relay board 22 placed on the side of the acoustic separation layer 34. When there is no relay board 22, the acoustic impedance of the acoustic separation layer 34 is set lower than the acoustic impedance of the electronic circuit board 20. By placing the resonance layer 30 being higher in acoustic impedance than the piezoelectric element 24 and the acoustic separation layer 34 being lower in acoustic impedance than the circuit board 16 adjacent to each other, a large difference in acoustic impedance is created at the boundary between the resonance layer 30 and the acoustic separation layer 34. With such a configuration, the ultrasound reflects at the boundary surface between the resonance layer 30 and the acoustic separation layer 34, and the amount of ultrasound propagating to the circuit board 16 is reduced. By setting the acoustic impedance of the resonance layer 30 to be higher than that of the piezoelectric element 24, and the acoustic impedance of the acoustic separation layer 34 to be lower than that of the relay board 22, the difference in acoustic impedance between the resonance layer 30 and the acoustic separation layer 34 can be increased.

The individual transducer 12 is connected to an electrode provided on a surface of the circuit board 16 via the acoustic separation layer 34. The resonance layer 30 and the acoustic separation layer 34 are set to be conductive, and the piezoelectric element 24 and the electrode of the circuit board 16 are electrically connected. The relay board 22 has a function to connect the individual transducer 12 and the electrode provided on an upper surface of the electronic circuit board 20, and, for example, the connection between the individual transducer 12 and the electrode is realized by a through via provided on the relay board 22. Placement of the wiring in the relay board 22 enables matching of differences in arrangement and a pitch between the electrode on the electronic circuit board 20 and the individual transducer 12. Alternatively, a circuit for switching the connection relationship between the electrode on the electronic circuit board 20 and the individual transducer 12 may be provided in the relay board 22.

As described above, the acoustic separation layer 34 is a layer for causing the ultrasound to be reflected at the boundary surface with the resonance layer 30 by the difference in the acoustic impedance with the resonance layer 30, and thus, must be formed from a material having a large difference in acoustic impedance from the resonance layer 30. As described above, the acoustic impedance of the resonance layer 30 is high, and thus, it is desirable to reduce the acoustic impedance of the acoustic separation layer 34, to achieve a large acoustic impedance difference. In addition, because electricity supplied from the circuit board 16 flows in the acoustic separation layer 34, a high conductivity is required for the acoustic separation layer 34. Further, because the acoustic separation layer 34 connects the individual transducer 12 and the circuit board 16, a high structural strength is also required. Thus, the acoustic separation layer 34 must have a low acoustic impedance, a high conductivity, and a high structural strength.

As a material which satisfies the above-described characteristics required for the acoustic separation layer 34, a porous material can be exemplified. For example, in production of a sintered conductive member, a pore ratio of 80 percent or greater can be achieved by mixing a binder or the like, and, with this process, the acoustic impedance can be set to be less than or equal to 1 MRayl. More specifically, as the material, a porous metal and porous carbon may be exemplified. Characteristics of a certain porous carbon are: an acoustic impedance of 0.7~1.0 MRayl, a specific resistance of about 2 to $20\times10^{-2}$ Ω cm, and a bending modulus of elasticity of 2 to 15 GPa, which satisfy the above-described required characteristics.

Figure 3:
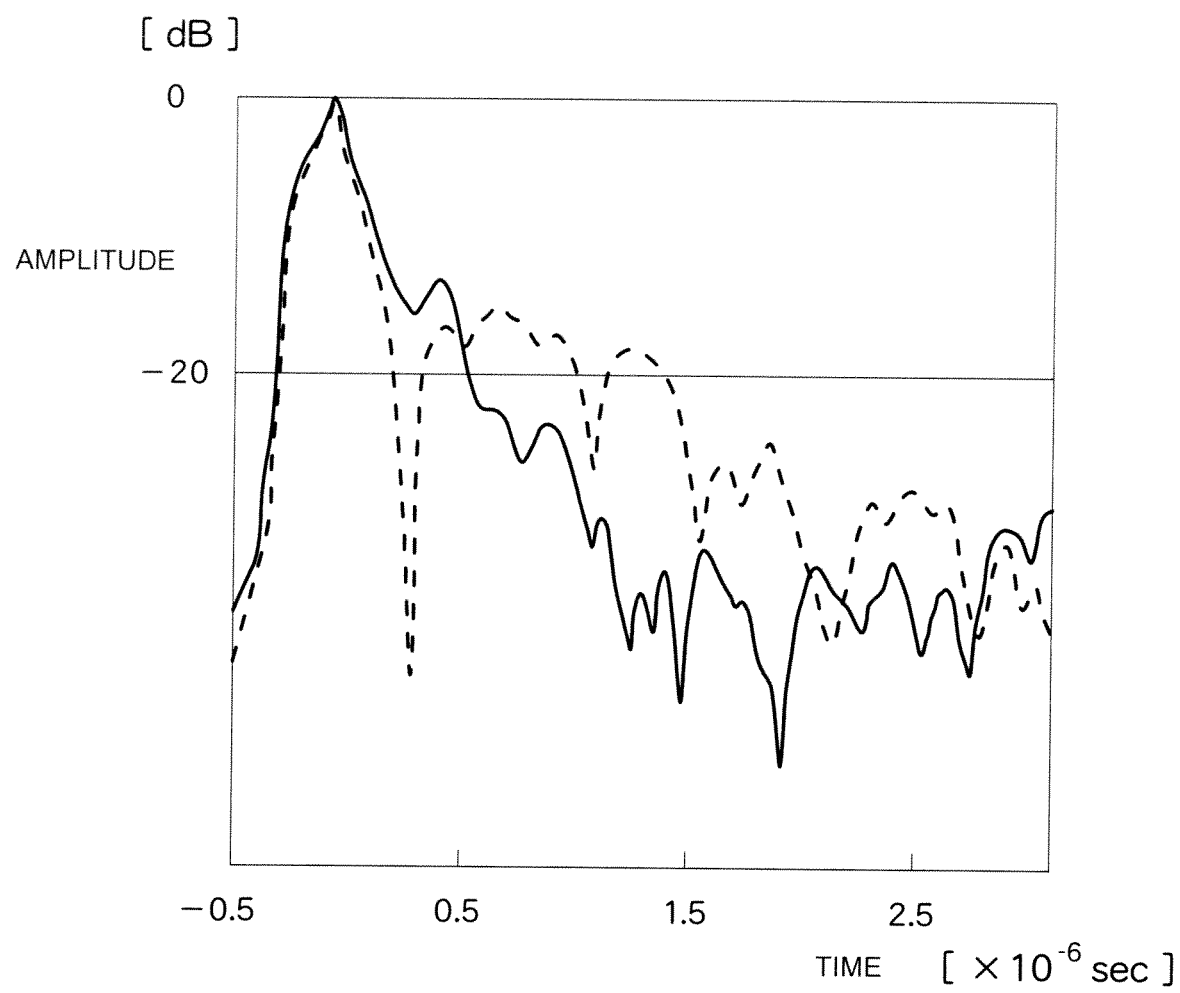
FIG. 3 is a diagram showing an effect of an acoustic separation layer.

FIG. 3 is a diagram showing an effect of the acoustic separation layer 34 made of porous carbon having the above-described characteristics. A horizontal axis shows elapsed time and a vertical axis shows an amplitude of ultrasound. A broken line shows a graph in a case where the acoustic separation layer 34 is not provided, and a solid line shows a graph in a case where the acoustic separation layer 34 is provided. FIG. 3 shows that a pulse width of the ultrasound at −20 dB became about 50 percent, indicating that the influence due to multiple reflections in a back layer of the acoustic separation layer 34 has been reduced. In the actual ultrasound image also, reduction of acoustic noise due to the multiple reflection is observed.

The acoustic impedance of the acoustic separation layer 34 made of the porous carbon is 1/20 that of the circuit board 16, and 1/100 to 1/70 that of the resonance layer 30. It is suggested that, with values lower than these values, the pulse width of the ultrasound may be reduced to 50 percent or less, and the image quality of the ultrasound image can be improved.

Employment of a configuration where the ultrasound is reflected at the boundary surface between the resonance layer 30 and the acoustic separation layer 34 enables improvement in the degree of freedom for selection of materials for the layers placed on the back side of the acoustic separation layer 34. In the structure of the related art having no acoustic separation layer 34, the noise has been suppressed by attenuating the ultrasound entering the layers behind the transducer element 26, such as the circuit board 16, within such layers. Thus, it has been necessary to select a material having a high attenuation for the material of these layers. By providing the acoustic separation layer 34, the ultrasound propagating to the layers behind the acoustic separation layer 34 can be reduced, and thus, it becomes possible to select a material with small attenuation.

REFERENCE SIGNS LIST

10 ULTRASOUND TRANSDUCER UNIT; 12 INDIVIDUAL TRANSDUCER; 16 CIRCUIT BOARD; 20 ELECTRONIC CIRCUIT BOARD; 22 RELAY BOARD; 24 PIEZOELECTRIC ELEMENT; 26 TRANSDUCER ELEMENT; 28 ACOUSTIC MATCHING LAYER; 30 RESONANCE LAYER; 34 ACOUSTIC SEPARATION LAYER.

The invention claimed is:

1. An ultrasound transducer unit comprising:
   a piezoelectric element;
   a circuit board having an electronic circuit which drives the piezoelectric element;
   a resonance layer placed between the piezoelectric element and the circuit board, and being higher in acoustic impedance than the piezoelectric element;
   an acoustic separation layer placed on a circuit board side of the resonance layer and adjacent to the resonance layer, and being lower in acoustic impedance than the circuit board, wherein
   the acoustic impedance of the acoustic separation layer is less than or equal to 1/70 of the acoustic impedance of the resonance layer; and
   an acoustic matching layer adjacent to the piezoelectric element and opposite the circuit board for gradationally reducing acoustic impedance from the piezoelectric element.

2. An ultrasound transducer unit comprising:
   a piezoelectric element;
   a circuit board having an electronic circuit which drives the piezoelectric element, and being lower in acoustic impedance than the piezoelectric element;
   a resonance layer placed between the piezoelectric element and the circuit board, and being higher in acoustic impedance than the piezoelectric element;
   an acoustic separation layer placed on a circuit board side of the resonance layer and adjacent to the resonance layer, and being lower in acoustic impedance than the circuit board, wherein
   the acoustic separation layer comprises a porous material; and
   an acoustic matching layer adjacent to the piezoelectric element and opposite the circuit board for gradationally reducing acoustic impedance from the piezoelectric element.

3. The ultrasound transducer unit according to claim 2, wherein
   the acoustic impedance of the acoustic separation layer is less than or equal to 1/70 of the acoustic impedance of the resonance layer.

4. An ultrasound transducer unit comprising:
   a piezoelectric element;
   a circuit board having an electronic circuit which drives the piezoelectric element, and being lower in acoustic impedance than the piezoelectric element;
   a resonance layer placed between the piezoelectric element and the circuit board, and being higher in acoustic impedance than the piezoelectric element; and
   an acoustic separation layer placed on a circuit board side of the resonance layer and adjacent to the resonance layer, and being lower in acoustic impedance than the circuit board, wherein
   the acoustic separation layer comprises porous carbon; and
   an acoustic matching layer adjacent to the piezoelectric element and opposite the circuit board for gradationally reducing acoustic impedance from the piezoelectric element.

5. The ultrasound transducer unit according to claim 4, wherein the acoustic impedance of the acoustic separation layer is less than or equal to 1/70 of the acoustic impedance of the resonance layer.

6. An ultrasound transducer unit comprising:
a piezoelectric element;
a circuit board having an electronic circuit which drives the piezoelectric element, and being lower in acoustic impedance than the piezoelectric element;
a resonance layer placed between the piezoelectric element and the circuit board, and being higher in acoustic impedance than the piezoelectric element;
an acoustic separation layer placed on a circuit board side of the resonance layer and adjacent to the resonance layer, and being lower in acoustic impedance than the circuit board, wherein
the acoustic impedance of the resonance layer is greater than or equal to 2.3 times the acoustic impedance of the piezoelectric element, and the acoustic impedance of the acoustic separation layer is less than or equal to 1/20 of the acoustic impedance of the circuit board; and
an acoustic matching layer adjacent to the piezoelectric element and opposite the circuit board for gradationally reducing acoustic impedance from the piezoelectric element.

7. The ultrasound transducer unit according to claim 6, wherein
the acoustic impedance of the acoustic separation layer is less than or equal to 1/70 of the acoustic impedance of the resonance layer.

* * * * *